US012697060B2

(12) United States Patent
Nauber et al.

(10) Patent No.: US 12,697,060 B2
(45) Date of Patent: Aug. 4, 2026

(54) INGESTIBLE ELECTROCHEMICAL SENSOR

(71) Applicant: Drägerwerk AG & Co. KGaA, Lübeck (DE)

(72) Inventors: Andreas Nauber, Lübeck (DE); Michael Sick, Lübeck (DE); Marie-Isabell Mattern-Frühwald, Lübeck (DE); Silja Dennier, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 209 days.

(21) Appl. No.: 18/727,373

(22) PCT Filed: Jan. 9, 2023

(86) PCT No.: PCT/DE2023/100008
§ 371 (c)(1),
(2) Date: Jul. 9, 2024

(87) PCT Pub. No.: WO2023/134827
PCT Pub. Date: Jul. 20, 2023

(65) Prior Publication Data
US 2025/0090083 A1      Mar. 20, 2025

(30) Foreign Application Priority Data

Jan. 11, 2022     (DE) ..................... 10 2022 100 522.4

(51) Int. Cl.
*A61B 5/00*          (2006.01)

(52) U.S. Cl.
CPC .......... *A61B 5/4255* (2013.01); *A61B 5/6861* (2013.01); *A61B 2562/162* (2013.01); *A61B 2562/168* (2013.01)

(58) Field of Classification Search
CPC ................ A61B 5/4255; A61B 5/6861; A61B 2562/268
See application file for complete search history.

(56) References Cited

U.S. PATENT DOCUMENTS

| | | |
|---|---|---|
| 10,326,139 B2 | 6/2019 | Kim et al. |
| 2010/0185055 A1 | 7/2010 | Robertson et al. |
| 2013/0091924 A1 | 4/2013 | Scheffler et al. |
| 2013/0289368 A1 | 10/2013 | Covington et al. |
| 2017/0276634 A1 | 9/2017 | Saffell et al. |
| 2020/0182823 A1 | 6/2020 | Porsgaard et al. |

FOREIGN PATENT DOCUMENTS

DE          102013101735 A1     10/2013

OTHER PUBLICATIONS

Yoshida, S., Miyaguchi, H. & Nakamura, T. (2018), Proof of Concept for Tablet-Shaped Ingestible Core-Body Thermometer with Gastric Acid Battery, IEEE Sensors Journal; 18(23), pp. 9755-9762; doi [Digital-Object-Identifier]: 10.1109/JSEN.2018.2871064.

*Primary Examiner* — Linda C Dvorak
*Assistant Examiner* — Abigail Bock
(74) *Attorney, Agent, or Firm* — McGlew and Tuttle, P.C.

(57) ABSTRACT
The present invention pertains to a swallowable electrochemical sensor, which is characterized in that its housing has electrolyte inlets, through which an aqueous electrolyte, for example, gastric acid, can enter from the area surrounding the sensor into the interior and act as an electrolyte there.

15 Claims, 3 Drawing Sheets

INGESTIBLE ELECTROCHEMICAL SENSOR

CROSS REFERENCE TO RELATED APPLICATIONS

This application is a United States National Phase Application of International Application PCT/DE2023/100008, filed Jan. 9, 2023, and claims the benefit of priority under 35 U.S.C. § 119 of German Application DE 10 2022 100 522.4, filed Jan. 11, 2022, the entire contents of which are incorporated herein by reference.

TECHNICAL FIELD

The present invention pertains to an electrochemical sensor, which is characterized in that it is swallowable (ingestible) and can be used for detecting gases in the intestinal tract of a person (human being).

BACKGROUND

Electrochemical sensors are known, in principle. They are electrochemical cells, which have at least one working electrode and a counterelectrode, and a flow of current can take place between the electrodes by means of a conductive liquid, the so-called electrolyte, if certain analytes enter into the area of the electrodes. The analytes are usually gases.

However, the drawback of common electrochemical sensors is that the materials which are usually needed for the electrochemical reaction, i.e., both the electrolyte and the electrodes, are often toxic or at least harmful for organisms.

The field of use of conventional electrochemical sensors is thus limited.

Nevertheless, it is of interest from a medical point of view to be able to detect certain gases within a body. It may thus be of interest, for example, in connection with inflammatory intestinal diseases, to monitor the formation of $H_2S$ or NO gas. For example, the degree of severity of a corresponding disease, which frequently occurs in waves, could be predicted on the basis of the formation of these gases.

Swallowable sensors are known, for example, from U.S. Pat. No. 10,326,139 B2. However, these are usually either optical sensors or pH sensors. These have only limited suitability for the detection of gases. Even though optical sensors can be used to detect methane at high concentrations, they are used more frequently for imaging the gastrointestinal tract. By contrast, pH sensors are used mainly for checking the pH value of the stomach.

Moreover, for example, a battery, which can be used for operating a swallowable electronic unit, is known from Yoshida, S., Miyaguchi, H. & Nakamura, T. (2018), *Proof of Concept for Tablet-Shaped Ingestible Core-Body Thermometer with Gastric Acid Battery*, IEEE Sensors Journal; 18(23), pp. 9755-9762; doi [Digital Object Identifier]: 10.1109/JSEN.2018.2871064. This battery is likewise an electrochemical cell. However, the electrodes are located in this case on the surface freely in the form of metal plates. The action as a battery develops as soon as these electrodes, located freely on the surface, come into contact with gastric juice from the environment. It should be noted that this is an electrochemical cell with gastric juice as the electrolyte, the general mode of operation is fundamentally different between batteries and electrochemical gas sensors. The battery proposed by Yoshida, S., Miyaguchi, H. & Nakamura, T. (2018) is consequently not suitable for the detection of gases at all.

SUMMARY

An object of the present invention is therefore to provide an electrochemical gas sensor for the detection of gases in the digestive tract of a person.

Principal features of the present invention are described herein. Embodiments are presented with this disclosure.

An electrochemical gas sensor with a housing, with at least one working electrode and with a counterelectrode is proposed, wherein the housing has a gas inlet, which is closed with a gas-permeable membrane. The electrochemical gas sensor is characterized in that the housing has at least one electrolyte inlet, which is filled with a hydrophilic sealant. The electrochemical gas sensor is preferably a swallowable gas sensor for detecting gases in the intestinal tract of a person.

Such a gas sensor can be swallowed by a person to be examined, so that it enters into the gastrointestinal tract. In other words, it is a swallowable sensor device. The hydrophilic sealant can then ensure in the gastrointestinal tract, preferably in the stomach, that gastric juice will enter the interior of the housing, preferably the interior space described below, through the electrolyte inlet. It is advantageous for this if the hydrophilic sealant is permeable to aqueous liquids, e.g., gastric juice, but offers a sealing effect against particles, for example, against food particles. The gastric juice can in this manner come into contact with the electrodes, especially with the working electrode and the counterelectrode and subsequently act as an electrolyte in the interior of the gas sensor. A fully functional electrochemical gas sensor is thus formed in the interior of the body of the person after the swallowing of the device according to the present invention due to the inflow of the gastric juice through the electrolyte inlet. In other words, the device according to the present invention can also be called a swallowable electrochemical instant gas sensor. This offers the great advantage that the use of conventional electrolytes, especially electrolytes that are toxic or harmful for health, can be eliminated by means of the device according to the present invention during the operation of the electrochemical gas sensor within the body of a person to be examined. This is a great advantage of the present invention.

In any case, the housing is a hollow body with an outer side and with an interior space. The components of the electrochemical cell are arranged in the interior space. In addition, the gastric juice acting as an electrolyte is located in the interior space in the ready-to-operate state.

It is favorable in this connection if the housing also has a gas inlet different from the electrolyte inlet. Gas to be detected can then enter through this gas inlet into the electrochemical cell and it can subsequently be reacted at the working electrode.

It is seen that it is thus advantageous if the housing has a plurality of openings, namely, at least one gas inlet and at least one electrolyte inlet. The gas inlet is a hole in the wall of the housing, through which gas can enter into the interior space of the housing. In order to prevent the entry of liquids through the gas inlet, it is useful if the gas inlet is closed with a membrane, which, though being permeable to gas, does, however, offer a barrier against liquid and particles. The electrolyte inlet is also a hole in the wall of the housing.

The gas can then come into contact in the interior space with the working electrode and with the electrolyte flowing in through the electrolyte inlet, as a result of which the electrochemical reaction will then take place. The electrochemical reaction leads to a flow of current between the working electrode and the counterelectrode. This flow of current can then be detected.

A measuring electronic unit is likewise arranged in the housing, preferably in an electronic space separate from the interior space in order to detect the electrochemical reaction. The measuring electronic unit is connected via precious metal wires to the electrodes of the electrochemical cell, which are arranged in the interior space. It can be configured to send a measured signal to a receiver, which is arranged outside the body of the person who has swallowed the sensor in a wireless manner, for example, via Bluetooth or a comparable wireless signal transmission.

The electrolyte inlet is an opening in the housing of the electrochemical sensor. The opening connects the interior of the housing to the outside environment of the electrochemical sensor. A liquid, preferably gastric juice, can flow through the opening into the interior of the housing.

The hydrophilic sealant is, for example, a glass nonwoven, hydrophilic PTFE (polytetrafluoroethylene), functionalized PO (polyolefin) or a similar material. Due to its hydrophilic property, it sucks gastric juice from the area surrounding the sensor. However, it also prevents at the same time larger particles from entering into the housing. The sealant thus ensures that the gastric juice is transported through the electrolyte inlet into the interior of the housing.

In other words, the present invention pertains to a swallowable electrochemical sensor, which is characterized in that its housing has electrolyte inlets, through which an aqueous electrolyte, for example, gastric juice, can enter into the interior from the area surrounding the sensor and act as an electrolyte there. The electrochemical sensor is thus changed over into the ready-to-operate state by the swallowing and by the entry of the gastric acid.

Provisions are made in a first embodiment variant for the interior of the housing to be filled with a hydrophilic filler. The hydrophilic filler can then act as a wick, which transports the gastric juice from the outer surrounding area of the swallowed sensor to the electrodes in a targeted manner. The hydrophilic filler may consist of the same material as the hydrophilic sealant as well. It can be ensured in this manner that the gastric juice acting as the electrolyte is not only sucked into the electrolyte inlet but actually fills the interior of the housing. In addition, it can be ensured by means of such a wick consisting of a hydrophilic material that the three-phase boundary necessary for an electrochemical reaction will be formed correctly for the detection of the gas. The wick, which is formed from the hydrophilic filler and fills the interior of the housing, thus ensures that, on the one hand, a sufficient quantity of electrolyte but also not an excessively large quantity of electrolyte is transported from the outside to the electrodes through the electrolyte inlet. The hydrophilic filler is preferably configured here such that the transportation of the electrolyte is influenced both by the hydrophilic nature of the material and by capillary forces. The strength of the acting capillary forces may be influenced, for example, by selecting the pore size of the filler. Glass fiber systems, e.g., glass fiber nonwoven, have proved to be especially suitable here as well.

It is, in addition, conceivable that the housing has a plurality of electrolyte inlet openings. This offers the advantage that the gastric juice has a plurality of possibilities for entering into the interior space of the housing. It is ensured in this manner that a sufficient quantity of gastric juice can enter into the interior space of the housing even in case one of the inlet openings is blocked by food particles or similar materials. It is also conceivable in this connection that all openings and the entire capsule are filled with hydrophilic fibers.

It is seen that it is favorable if the sensor is a capsule. A capsule is defined here, in general, as a usually small, round container, which can be used for transporting objects that are to be protected. Such a container usually has a housing and the object to be transported is arranged in the interior said housing. The housing of the capsule may form the housing of the electrochemical sensor in this case, and the rest of the configuration of the sensor corresponds otherwise to the description already given above and to the description to be given below. It is also conceivable, as an alternative, that the sensor is in the form of a tablet. In any case, the sensor may be called an encapsulated sensor.

It is conceivable that the housing consists of an inert plastic. For example, the housing may be manufactured from polypropylene or polyethylene suitable for medical use. An inert material reacts, if it does react at all, with reagents and substances present in the surrounding area to a negligibly low extent only and it does not preferably react at all. It is seen that it is especially favorable if the inert plastic is a plastic that is inert with respect to gastric juice. A plastic that is inert with respect to gastric juice is inert especially with respect to hydrochloric acid and digestive enzymes.

The sensor could also have, in addition, a soft, inert material as an envelope. Such an envelope may be applied, for example, as a coating on the outside of the housing. This envelope may be used to improve the swallowability of the sensor. It is conceivable, for example, that the envelope consists of silicone or another, medically inert material. A medically inert material is in this case a material that does not react with body fluids, for example, gastric juice or other digestive enzymes and is also not resorbed in the body but is excreted in an unchanged form. If the envelope is formed from a corresponding resistant and inert material, it is, of course, configured such that it does not close the inlet openings in the housing, i.e., the gas inlet and the electrolyte inlet.

As an alternative, the sensor could also have an envelope consisting of a soft and resorbable material. Such a soft and resorbable material could be, for example, gelatin. The swallowability of the sensor can also be improved further with such an envelope. The resorbable material may be dissolved, for example, by the gastric juices. It is also possible in this case that the envelope at first covers the inlet openings in the housing. This may be, for example, favorable for the manufacturing process. The sensor could then be dipped simply completely in gelatin.

In any case, it is useful if the gas inlet is located directly in front of the working electrode. The section over which the gas has to travel within the sensor until it is reacted at the working electrode can be kept short in this manner. It is advantageous in this connection if a hydrophobic membrane is arranged in front of the gas inlet in front of the working electrode. Such a membrane may be used, on the one hand, as a physical barrier and prevent the entry of food particles. On the other hand, the hydrophobic membrane can prevent the entry of gastric juice through the gas inlet. The hydrophobic membrane may be configured as a porous membrane in order to make the entry of other materials other than gas additionally difficult. A porous membrane is defined here as a membrane with a pore size of at most 5 μm. It is favorable in this connection if the pore size is smaller than 5 μm, preferably smaller than 4 μm, especially preferably smaller than 3 μm and especially preferably even equal to 2 μm or smaller.

In addition to the working electrode and the counterelectrode, the sensor may also have a reference electrode. The reference electrode is likewise arranged in the interior space of the housing and it comes likewise into an electrically conductive contact in this manner with the electrolyte. It may be used to calibrate and test the operability of the sensor according to the present invention. This is especially advantageous because the swallowed sensor is not readily accessible from the outside for calibration or maintenance.

In any case, the electrode material may be selected from among palladium, platinum, rhodium, iridium, carbon and/ or gold. Mixtures of the above-mentioned materials are conceivable as well. Carbon and gold, in particular, offer the additional advantage of being inert materials. The other electrode materials may also be used without hesitation based on the configuration according to the present invention of the sensor, because they are located entirely in the interior of the sensor and cannot consequently come into contact with tissues of the body. It is seen that the configuration of the sensor as encapsulated sensor offers an additional advantage in this respect.

It is also conceivable in this connection that two working electrodes are present. This is advantageous, for example, when a plurality of different gases are to be detected. Thus, the first working electrode may consist, for example, of iridium. Such an iridium electrode can be used selectively for detecting $H_2S$. The second working electrode may consist of carbon. A carbon electrode can then be used for the selective detection of NO. A sensor, which has a first working electrode consisting of iridium and a second working electrode consisting of carbon, can thus be used for the selective detection of $H_2S$ and NO. This is helpful, for example, when an incipient wave of inflammation shall be detected in the course of a chronic colitis.

It is conceivable in one embodiment variant that the sensor can be filled with an electrolyte, the electrolyte being selected from the group comprising citric acid, formic acid, acetic acid, hydrochloric acid or phosphoric acid. The sensor may be filled with the electrolyte, for example, especially before swallowing. The sensor provided, which is free from electrolyte, is placed for this purpose into an electrolyte bath. The electrolyte bath consists, for example, of a solution consisting of citric acid, formic acid, acetic acid or the like. It is especially favorable if the electrolyte bath consists of a citric acid solution. The citric acid is preferably an aqueous solution, the citric acid being preferably present in a concentration in the range of 0.1 M to 2 M, preferably 0.5 M to 1 M, and especially preferably 0.75 M. It is especially favorable in another embodiment variant if the electrolyte bath consists of a hydrochloric acid solution. The hydrochloric acid solution is an aqueous solution, the hydrochloric acid being present in a concentration range of 0.1 M to 2 M, preferably 0.5 M to 1 M, and especially preferably 1 M. It is obvious that small tolerances of the concentration range likewise belong to the corresponding exemplary embodiments. It is especially favorable in yet another embodiment variant if the electrolyte bath consists of a phosphoric acid solution. The phosphoric acid solution is an aqueous solution, the phosphoric acid being present in a concentration range of 0.1 M to 2 M, preferably 0.5 M to 1 M, and especially preferably 1 M. It is obvious that small tolerances of the concentration range likewise belong to the corresponding exemplary embodiments in this case as well.

It is seen that a process for providing a swallowable electrochemical sensor is also advantageous in the sense of the present invention, wherein the process comprises the following steps:

a. provision of an unfilled electrochemical sensor,
   b. provision of an electrolyte solution,
   c. bathing of the unfilled electrochemical sensor in the electrolyte solution, and
   d. provision of the prefilled electrochemical sensor.

The sensor may optionally also be provided here with a coating between the steps c and d, i.e., after it had been prefilled by the bath in the electrolyte solution and before it is provided for swallowing. For example, the coating with gelatin, already described above, may be applied. Other coating materials are, of course, conceivable as well. The process may thus also comprise the following step e:

e. coating of the prefilled sensor with a layer dissolving spontaneously in contact with gastric acid.

Step e is preferably carried out after step c but before step d.

In any case, it is favorable if the prefilling of the electrochemical sensor corresponding to step c also includes a brief rinsing of the sensor after bathing the unfilled electrochemical sensor. The rinsing may take place, for example, by a brief rinsing under running water immediately before swallowing. It is, however, preferable to dip the sensor bathed in the electrolyte solution briefly into a rinsing bath. The rinsing bath may contain, for example, distilled water or a physiological saline solution.

It is especially favorable if the electrolyte bath provided corresponding to step b has an electrolyte, which is selected from the group containing citric acid, formic acid, acetic acid, hydrochloric acid, phosphoric acid, preferably citric acid, formic acid, hydrochloric acid or phosphoric acid, and especially preferably citric acid, hydrochloric acid or phosphoric acid.

It is conceivable in this connection, for example, that the unfilled sensor is made at first available to a medical or pharmaceutical staff. The staff will then carry out the steps necessary for the preparation and the coating of the sensor. The coating may be carried out, for example, by dipping the prefilled sensor into a gelatin solution or the like. The staff can then hand over the sensor thus prepared to a patient, who will then swallow it.

After swallowing, gastric acid can then flow into the sensor through one or more electrolyte inlets in addition to the electrolyte already present in the sensor, as it was already described above.

In another advantageous embodiment variant, the solution according to the object consequently also contains a kit for detecting intestinal gases, the kit having an unfilled electrochemical sensor corresponding to the above-described sensor, as well as an electrolyte preparation.

It is conceivable in this connection that the electrolyte preparation is present as a ready-to-use liquid preparation, as a concentrated liquid preparation or as a powder. Using the kit, medical or pharmaceutical staff or even a patient himself/herself can correspondingly prefill the swallowable electrochemical sensor himself/herself immediately before use. If the electrolyte preparation is in the form of a powder, it can be dissolved, for example, in a correspondingly predefined quantity of liquid. For example, it can be dissolved in a quantity of tap water or distilled water predefined in the instructions for use. If the electrolyte preparation is in the form of a concentrated liquid preparation, it can be diluted prior to the bathing of the unfilled sensor in the electrolyte preparation corresponding to the information in the instructions for use until the desired concentration to be used is reached.

Moreover, such a kit may also provide a corresponding rinsing solution. It is also conceivable that the kit comprises corresponding vessels, in which the electrolyte preparation and the rinsing solution can be provided for dipping the sensor.

Further features, details and advantages of the present invention appear from the text of the claims as well as from the following description of exemplary embodiments on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
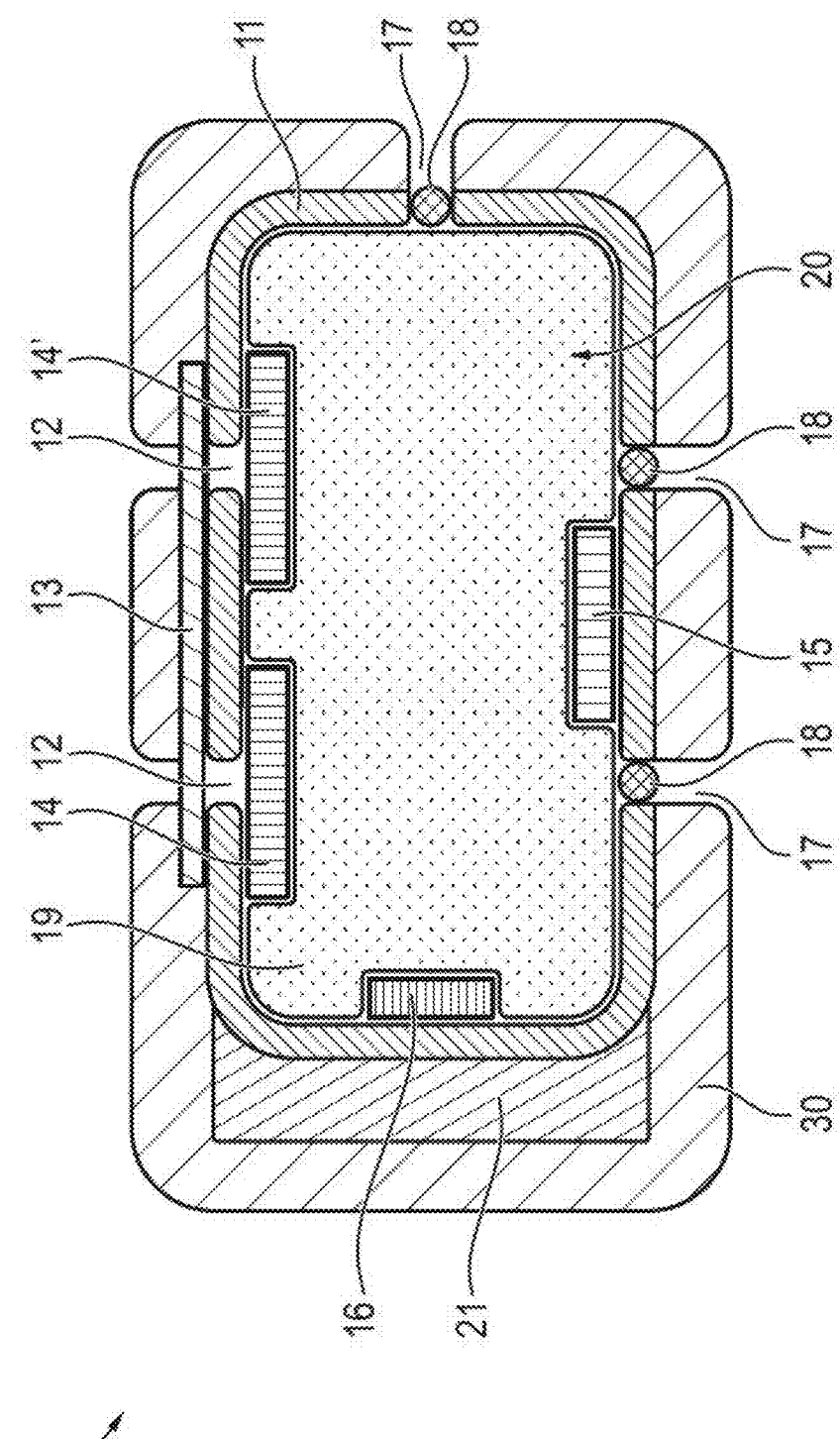
FIG. 1 is a schematic cross sectional view through a sensor according to the present invention.
Figure 2:
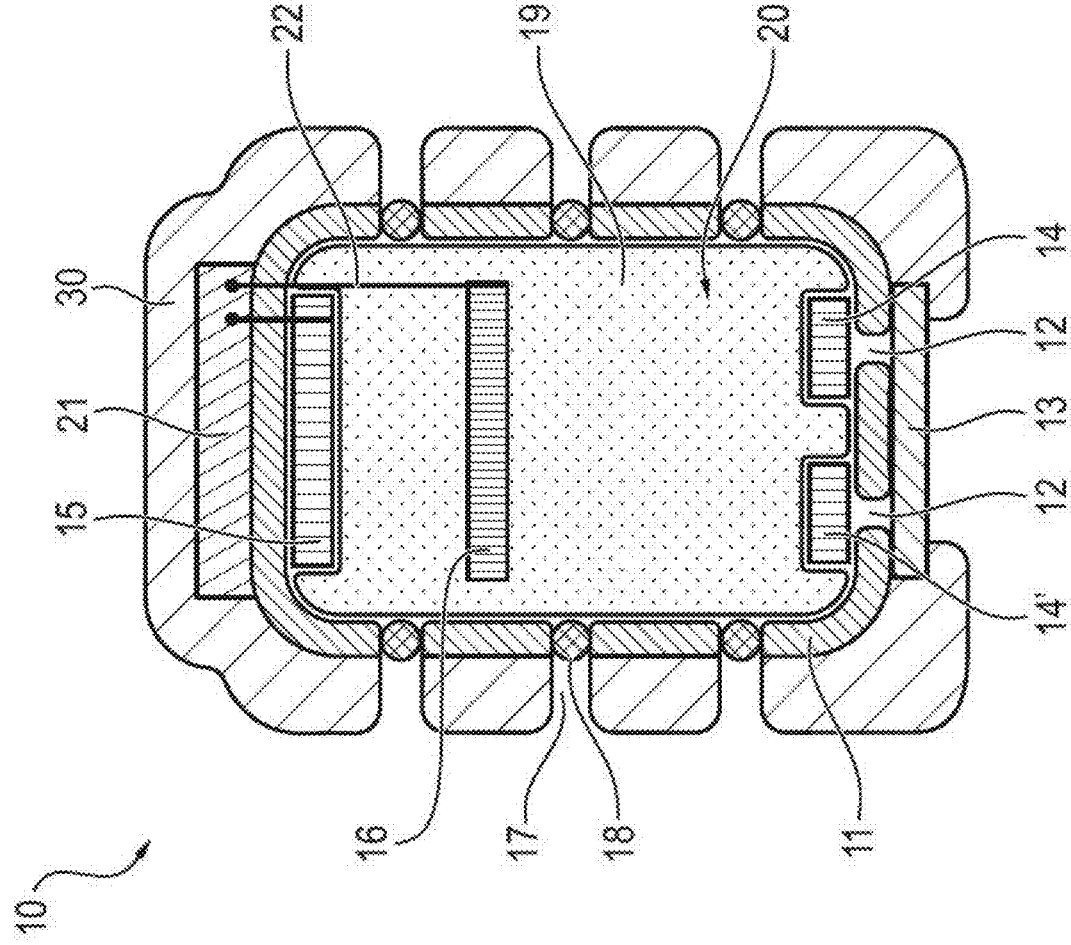
FIG. 2 is another schematic cross sectional view through a sensor according to the present invention.

Referring to the drawings, a cross section through a gas sensor 10 is seen both in FIG. 1 and in FIG. 2. The gas sensor 10 has a housing 11. The housing 11 has an interior space 20. A first working electrode 14 and a second working electrode 14' are arranged in the interior space 20. Embodiments that have only one working electrode 14 are conceivable as well. Furthermore, a counterelectrode 15 as well as a reference electrode 16 are arranged in the interior space 20.

An electronic unit 21 is arranged on the outside of the housing 11. The electronic unit 21 is installed in a sealed capsule. The electrodes 14, 14', 15, 16 are in connection with the electronic unit 21 via wire connections 22, which are led out of the electronic unit 21 and through the housing 11, as it can be seen especially in FIG. 2. This wire connection cannot be seen for all electrodes in FIGS. 1 and 2, because it is partially located outside the cross-sectional plane of the view. However, there is, of course, a corresponding wire connection 22 for each of the electrodes.

It is seen that the housing 11 has a plurality of openings, namely, openings that are used as a gas inlet 12, and openings that are used as an electrolyte inlet 17.

The gas inlet 12 is always arranged such that a working electrode 14, 14' is located directly behind the gas inlet 12 on the inside of the housing 11. In addition, each gas inlet 12 is closed by a hydrophobic membrane 13, Only gas can enter into the sensor and reach the working electrode 14, 14' in this manner through the gas inlet 12. Aqueous liquids are repelled based on the hydrophobic property of the membrane. Solid particles, e.g., food particles, are prevented from entering by the physical barrier effect of the membrane. The hydrophobic membrane 13 is located on the outside of the housing 12 in the example shown in FIGS. 1 and 2. It is also conceivable that it is arranged on the inside of the housing 12, but the embodiment shown in the figures is nevertheless preferred. Furthermore, it is seen that a hydrophobic membrane 13 covers all gas inlets 12 in FIGS. 1 and 2. It is, of course, also conceivable that each gas inlet 12 is closed with a hydrophobic membrane 13 each, and the embodiment variant shown in the figures is preferred in this case as well.

The openings, which are used as electrolyte inlets 17, are each provided with hydrophilic seals 18. Based on their hydrophilic properties, these guide aqueous liquids into the interior space 20 of the housing 11. However, just like the hydrophobic membrane 13, the hydrophilic seals 18 prevent solid particles from being able to enter the interior space 20.

The interior space 20 of the housing 11 is filled, furthermore, with a hydrophilic filler 19. This filler 19 may act as a sponge or as a wick and support in this manner, for example, the entry of the gastric acid acting as an electrolyte. Furthermore, the hydrophilic filler 19 can maintain the electrolyte, which has entered successfully, in the interior space 20 of the housing 11.

It is further seen in FIGS. 1 and 2 that the entire device 10 is enclosed by an envelope 30. The envelope 30 forms a capsule around the sensor 10. The envelope 30 consists, for example, of a soft, inert material, as was described above. It is seen that the envelope 30 also encloses the hydrophobic membrane. The envelope 30 likewise has passage openings only at the locations at which the gas inlets 12 and the electrolyte inlets 17 are formed.

Figure 3:
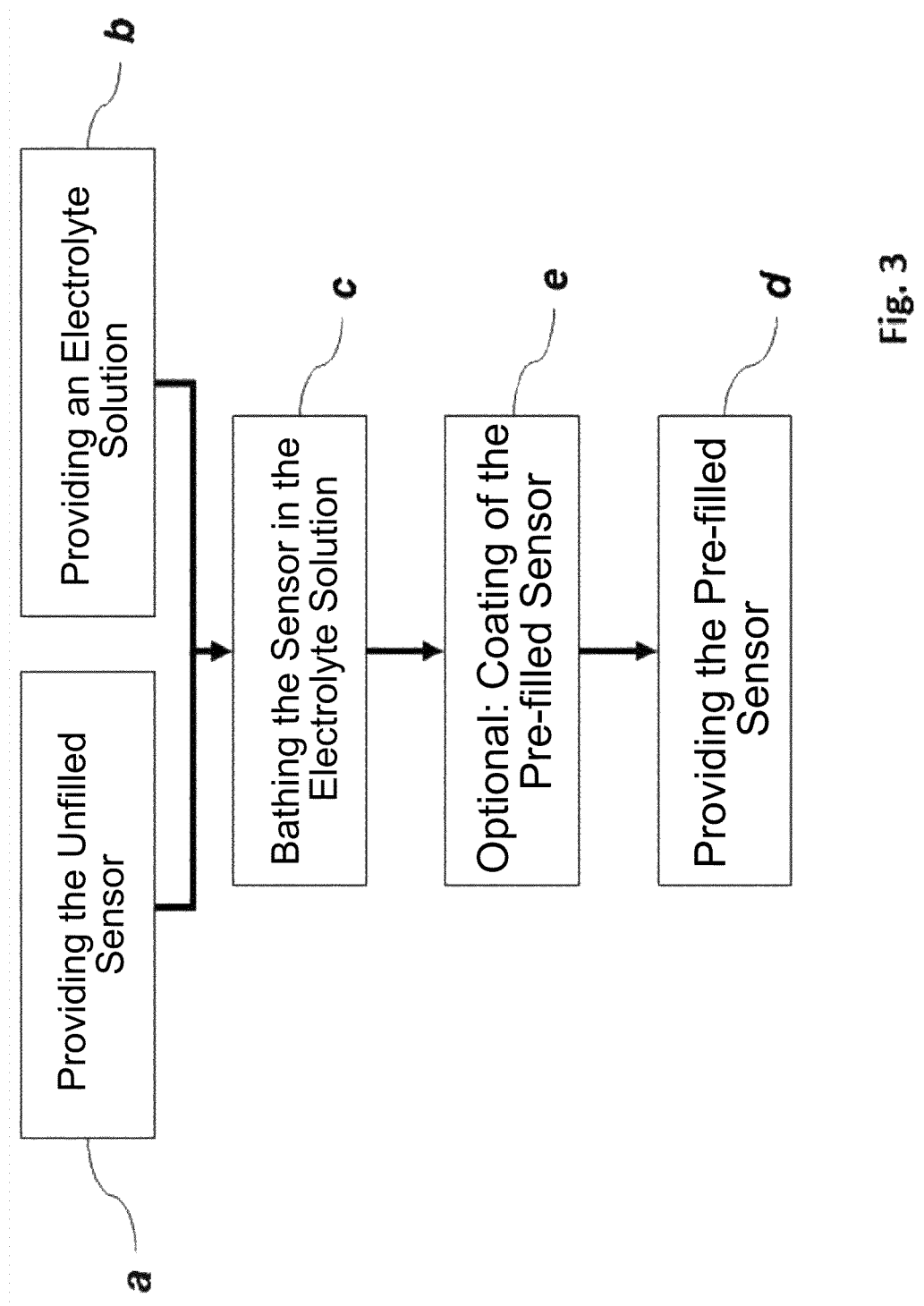
FIG. 3 is a schematic overview of a process for providing a swallowable electrochemical sensor.

It is seen in FIG. 3 that a corresponding swallowable electrochemical sensor can be provided, in which an unfilled sensor 10 is provided in a first step a. This unfilled sensor 10 corresponds to the above-described sensor 10 shown in FIGS. 1 and 2. In order to avoid repetitions, reference is thus made for all features of the unfilled sensor 10 provided to the above-described feature. An electrolyte solution is provided in a further step b. This electrolyte solution may contain, for example, citric acid, formic acid or acetic acid as an electrolyte. Corresponding to step c of the process, the unfilled sensor 10 provided is then bathed in the electrolyte solution provided. The sensor is prefilled now with the corresponding electrolyte. Corresponding to step e, the sensor 10 thus prefilled may optionally be provided in step e with a coating when needed before it is made available for further use in any case corresponding to step d.

The electrolyte solution provided corresponding to step b is a solution of 0.75 M citric acid in water in a preferred exemplary embodiment.

The electrolyte solution provided corresponding to step b is an aqueous solution of 1 M hydrochloric acid in another exemplary embodiment.

The electrolyte solution provided corresponding to step b is an aqueous solution of 1 M phosphoric acid in yet another exemplary embodiment.

The present invention is not limited to one of the above-described embodiments, but it can be varied in many different ways.

All the features and advantages described in the claims, in the specification and in the drawings, including design details, arrangements in space and process steps, may be essential for the present invention both in themselves and in the different combinations.

In any case, provisions are made in an electrochemical sensor 10 with a housing 11, with at least one working electrode 14 and with a counterelectrode 15, wherein the housing 11 has an interior space 20, in which the working electrode 14 and the counterelectrode 15 are arranged, and wherein the housing 11 has at least one gas inlet 12, wherein each gas inlet 12 is connected to a gas-permeable membrane 13, for the housing 13 to have at least one electrolyte inlet 17, wherein each electrolyte inlet 17 is filled with a hydrophilic sealant 18. It is favorable here if the interior space 20 of the housing 11 is filled with a hydrophilic filler 19 and/or if the housing 11 has a plurality of electrolyte inlet openings 17. It is also advantageous if the sensor 10 is a capsule, if the housing 11 consists of an inert plastic and/or if the sensor 10 has a soft, inert material as the envelope 30. The gas inlet 12 is advantageously located directly in front of the working electrode 14, and a hydrophobic membrane 13 is arranged in front of the gas inlet 12.

Furthermore, it is favorable if the sensor 10 has a reference electrode 16. The electrode material may be selected from among palladium, platinum, rhodium, iridium, carbon and/or gold. Two working electrodes 14, 14' are preferably present. The first working electrode 14 may consist of iridium. The second working electrode 14' may consist of carbon.

While specific embodiments of the invention have been shown and described in detail to illustrate the application of the principles of the invention, it will be understood that the invention may be embodied otherwise without departing from such principles.

LIST OF REFERENCE NUMBERS

10 Gas sensor
11 Housing
12 Gas inlet
13 Hydrophobic membrane
14 Working electrode
14' Working electrode
15 Counterelectrode
16 Reference electrode
17 Electrolyte inlet
18 Hydrophilic sealant
19 Hydrophilic filler
20 Interior space
21 Electronic unit
22 Wire connection
30 Envelope

The invention claimed is:

1. A swallowable electrochemical sensor for detecting gases in the intestinal tract of a person, the electrochemical sensor comprising:
a housing;
at least one working electrode;
a counterelectrode;
a gas-permeable membrane; and
a hydrophilic sealant,
wherein the housing has an interior space, in which the working electrode and the counterelectrode are arranged,
wherein the housing has at least one gas inlet,
wherein the at least one gas inlet is closed with the gas-permeable membrane,
wherein the housing has at least one electrolyte inlet, and
wherein the at least one electrolyte inlet is filled with the hydrophilic sealant.

2. An electrochemical sensor in accordance with claim 1, further comprising a hydrophilic filler, wherein the interior space of the housing is filled with the hydrophilic filler.

3. An electrochemical sensor in accordance with claim 1, wherein the housing has a plurality of electrolyte inlet openings.

4. An electrochemical sensor in accordance with claim 1, wherein the sensor is comprises a capsule.

5. An electrochemical sensor in accordance with claim 1, wherein the housing is formed of an inert plastic.

6. An electrochemical sensor in accordance with claim 1, further comprising a soft, inert material configured as an envelope.

7. An electrochemical sensor in accordance with claim 1, wherein the gas inlet is located directly in front of the working electrode.

8. An electrochemical sensor in accordance with claim 1, wherein the gas-permeable membrane comprises a hydrophobic membrane is arranged in front of the gas inlet in front of the working electrode.

9. An electrochemical sensor in accordance with claim 1, further comprising another working electrode such that two working electrodes are present.

10. An electrochemical sensor in accordance with claim 1, wherein the sensor is configured to be filled with an electrolyte, wherein the electrolyte is selected from the group comprising citric acid, formic acid, acetic acid, hydrochloric acid and phosphoric acid.

11. A process for providing a swallowable electrochemical sensor, the electrochemical sensor comprising: a housing; a working electrode; a counterelectrode; a gas-permeable membrane; and a hydrophilic sealant, wherein the housing comprises an interior space, in which the working electrode and the counterelectrode are arranged, and the housing comprises a gas inlet closed with the gas-permeable membrane, and the housing comprises an electrolyte inlet filled with the hydrophilic sealant, the process comprising the steps of:
a. providing the electrochemical sensor as an unfilled electrochemical sensor;
b. providing an electrolyte solution;
c. bathing the unfilled electrochemical sensor in the electrolyte solution;
d. providing the electrochemical sensor as prefilled electrochemical sensor.

12. A process in accordance with claim 11, wherein the process additionally comprises the following step:
e. coating of the prefilled electrochemical sensor with a layer that dissolves spontaneously on contact with gastric acid.

13. A process in accordance with claim 11, wherein the electrolyte bath provided corresponding to step b has an electrolyte, which is selected from the group comprising citric acid, formic acid, acetic acid, hydrochloric acid, phosphoric acid.

14. A kit for detecting intestinal gases, the kit comprising:
an electrochemical sensor, the electrochemical sensor comprising a working electrode; a counterelectrode; a gas-permeable membrane; a hydrophilic sealant and a housing, the housing comprising an interior space, in which the working electrode and the counterelectrode are arranged, a gas inlet closed with the gas-permeable membrane, and an electrolyte inlet filled with the hydrophilic sealant, wherein the electrochemical sensor is an unfilled electrochemical sensor; and
an electrolyte preparation.

15. A kit in accordance with claim 14, wherein the electrolyte preparation is in a form of a ready-to-use liquid preparation, a concentrated liquid preparation or a powder.

* * * * *